(12) United States Patent
Wolf et al.

(10) Patent No.: US 8,094,315 B2
(45) Date of Patent: *Jan. 10, 2012

(54) METHODS FOR MAKING AND USING SPR MICROARRAYS

(75) Inventors: Nicholas Adam Wolf, Woodinville, WA (US); Danliang Jin, Bothell, WA (US); Anna Barklund, Kirkland, WA (US); Raluca Dinu, Redmond, WA (US)

(73) Assignee: Plexera LLC, Woodinville, WA (US)

( * ) Notice: Subject to any disclaimer, the term of this patent is extended or adjusted under 35 U.S.C. 154(b) by 318 days.

This patent is subject to a terminal disclaimer.

(21) Appl. No.: 12/330,384

(22) Filed: Dec. 8, 2008

(65) Prior Publication Data

US 2009/0093067 A1 Apr. 9, 2009

Related U.S. Application Data

(62) Division of application No. 11/296,659, filed on Dec. 6, 2005, now Pat. No. 7,463,358.

(51) Int. Cl.
*G01N 21/55* (2006.01)
(52) U.S. Cl. ....... 356/445; 356/448; 422/69; 435/288.7; 436/164; 428/615; 428/621; 428/624; 428/630; 428/668; 428/446
(58) Field of Classification Search .................. None
See application file for complete search history.

(56) References Cited

U.S. PATENT DOCUMENTS

| | | | |
|---|---|---|---|
| 3,105,902 A | 10/1963 | Ostrofsky |
| 3,751,587 A | 8/1973 | Insler |
| 3,891,507 A | 6/1975 | Breuer |
| 3,990,850 A | 11/1976 | Friedman |
| 4,038,030 A | 7/1977 | Albright |
| 4,148,057 A | 4/1979 | Jesse |
| 4,375,025 A | 2/1983 | Carlson |
| 4,585,931 A | 4/1986 | Duncan |
| 4,638,144 A | 1/1987 | Latta |
| 4,707,722 A | 11/1987 | Folk |
| 4,719,502 A | 1/1988 | Ikeya |
| 4,753,863 A | 6/1988 | Spanjer |
| 4,789,804 A | 12/1988 | Karube |
| 4,861,620 A | 8/1989 | Azuma |
| 4,945,045 A | 7/1990 | Forrest |
| 4,945,204 A | 7/1990 | Nakamura |
| 4,997,278 A | 3/1991 | Finlan |
| 5,030,551 A | 7/1991 | Herren |
| 5,068,124 A | 11/1991 | Batey |
| 5,078,855 A | 1/1992 | Mochizuki |
| 5,089,112 A | 2/1992 | Skotheim |
| 5,104,619 A | 4/1992 | de Castro |
| 5,116,481 A | 5/1992 | Ozawa |
| 5,157,412 A | 10/1992 | Kleinschmick |
| 5,192,507 A | 3/1993 | Taylor |
| 5,200,051 A | 4/1993 | Cozzette |
| 5,206,280 A | 4/1993 | Williams |
| 5,242,828 A | 9/1993 | Bergstrom |
| 5,246,846 A | 9/1993 | Pittner |
| 5,262,470 A | 11/1993 | Shimotsuma |
| 5,268,305 A | 12/1993 | Ribi |
| 5,313,264 A | 5/1994 | Ivarsson |
| 5,329,090 A | 7/1994 | Woelki |
| 5,346,802 A | 9/1994 | Ohbachi |
| 5,357,077 A | 10/1994 | Tsuruta |
| 5,368,712 A | 11/1994 | Tomich |
| 5,373,039 A | 12/1994 | Sakai |
| 5,401,378 A | 3/1995 | King |
| 5,405,783 A | 4/1995 | Pirrung |
| 5,413,629 A | 5/1995 | Yasui |
| 5,415,838 A | 5/1995 | Rieger |
| 5,436,161 A | 7/1995 | Bergstrom |
| 5,436,170 A | 7/1995 | Cornell |
| 5,445,923 A | 8/1995 | Takahashi |
| 5,445,934 A | 8/1995 | Fodor et al. |
| 5,474,796 A | 12/1995 | Brennan |
| 5,478,756 A | 12/1995 | Gizeli |
| 5,485,277 A | 1/1996 | Foster |
| 5,491,097 A | 2/1996 | Ribi |
| 5,492,840 A | 2/1996 | Malmqvist |
| 5,512,131 A | 4/1996 | Kumar |

(Continued)

FOREIGN PATENT DOCUMENTS

DE 10064146 12/2000

(Continued)

OTHER PUBLICATIONS

"Influence of Multilayer Coating Peculiarities on Efficiency of Surface Plasmon Resonance Photodetector" authored by Mayeva et al., and published in the Proceedings of the International Semiconductor Conference 1998 (CAS '98), Sanaia, Romania, Oct. 6-10, 1998, vol. 2, p. 531-534 IEEE.*

"Surface Plasmon Resonance (SPR)," BMS, http://www.bmskorea.co.kr.bms_Product/bms_Product_Main.aspx?sec=detail&num=2811, printed Nov. 15, 2005, 6 pages.

Hyun et al., "Enzymatic Nanolithography of a Self-Assembled Oligonucleotide Monolayer on Gold," J. Am. Chem. Soc., 2004, 126:4770-4771.

(Continued)

*Primary Examiner* — Marc Zimmer

(74) *Attorney, Agent, or Firm* — Sci-Law Strategies, PC

(57) ABSTRACT

An article, process, and method for surface plasmon resonance plates are described. A substrate is covered with a thin metal film onto which a second thin metal film is deposited. The surface of the second thin metal film is converted to the metal oxide which is used to covalently bond organosilanes to the surface. Reactive organosilanes containing terminal bonding groups are arranged in a plurality of spots that are surrounded by inert organosilanes. Biomolecule attachment to the binding group is detected or measured from surface plasmon signals from the first thin metal film.

10 Claims, 4 Drawing Sheets

U.S. PATENT DOCUMENTS

| | | |
|---|---|---|
| 5,514,501 A | 5/1996 | Tarlov |
| 5,527,711 A | 6/1996 | Tom-Moy |
| 5,536,822 A | 7/1996 | Haystead |
| 5,567,301 A | 10/1996 | Stetter |
| 5,571,568 A | 11/1996 | Ribi |
| 5,580,794 A | 12/1996 | Allen |
| 5,622,872 A | 4/1997 | Ribi |
| 5,624,537 A | 4/1997 | Turner |
| 5,629,790 A | 5/1997 | Neukermans |
| 5,637,201 A | 6/1997 | Raguse |
| 5,688,642 A | 11/1997 | Chrisey |
| 5,693,477 A | 12/1997 | Cornell |
| 5,707,502 A | 1/1998 | McCaffrey |
| 5,716,778 A | 2/1998 | Weng |
| 5,719,060 A | 2/1998 | Hutchens |
| 5,723,345 A | 3/1998 | Yamauchi |
| 5,736,410 A | 4/1998 | Zarling |
| 5,741,409 A | 4/1998 | Raguse |
| 5,753,093 A | 5/1998 | Raguse |
| 5,756,355 A | 5/1998 | Lang |
| 5,783,054 A | 7/1998 | Raguse |
| 5,798,030 A | 8/1998 | Raguse |
| 5,824,483 A | 10/1998 | Housten |
| 5,834,224 A | 11/1998 | Ruger |
| 5,844,099 A | 12/1998 | Stahl |
| 5,846,842 A | 12/1998 | Herron |
| 5,922,594 A | 7/1999 | Lof |
| 5,922,617 A | 7/1999 | Wang |
| 5,938,595 A | 8/1999 | Glass |
| 5,942,388 A | 8/1999 | Willner |
| 5,955,379 A | 9/1999 | Lennox |
| 5,985,377 A | 11/1999 | Corbet |
| 6,020,208 A | 2/2000 | Hutchens |
| 6,027,942 A | 2/2000 | Hutchens |
| 6,040,193 A | 3/2000 | Winkler et al. |
| 6,054,270 A | 4/2000 | Southern |
| 6,074,616 A | 6/2000 | Beuchler |
| 6,096,825 A | 8/2000 | Garnier |
| 6,101,946 A | 8/2000 | Martinsky |
| 6,113,992 A | 9/2000 | Corbet |
| 6,146,593 A | 11/2000 | Pinkel |
| 6,150,147 A | 11/2000 | Goldberg et al. |
| 6,165,335 A | 12/2000 | Lennox et al. |
| 6,197,599 B1 | 3/2001 | Chin |
| 6,217,949 B1 | 4/2001 | Corbet |
| 6,218,111 B1 | 4/2001 | Southern et al. |
| 6,218,194 B1 | 4/2001 | Lyndin |
| 6,219,138 B1 | 4/2001 | Swanson |
| 6,225,047 B1 | 5/2001 | Hutchens |
| 6,225,625 B1 | 5/2001 | Pirrung et al. |
| 6,232,066 B1 | 5/2001 | Felder |
| 6,245,590 B1 | 6/2001 | Wine |
| 6,261,776 B1 | 7/2001 | Pirrung et al. |
| 6,291,155 B1 | 9/2001 | Raguse |
| 6,291,183 B1 | 9/2001 | Pirrung et al. |
| 6,309,831 B1 | 10/2001 | Goldberg et al. |
| 6,322,970 B1 | 11/2001 | Little |
| 6,329,209 B1 | 12/2001 | Wagner |
| 6,340,597 B1 | 1/2002 | Svorc |
| 6,346,413 B1 | 2/2002 | Fodor et al. |
| 6,362,912 B1 | 3/2002 | Lewis |
| 6,379,929 B1 | 4/2002 | Burns |
| 6,380,365 B1 | 4/2002 | Akerstrom |
| 6,399,365 B2 | 6/2002 | Besemer et al. |
| 6,406,921 B1 | 6/2002 | Wagner |
| 6,416,952 B1 | 7/2002 | Pirrung et al. |
| 6,421,164 B2 | 7/2002 | Tearney |
| 6,433,907 B1 | 8/2002 | Lippert |
| 6,447,723 B1 | 9/2002 | Schermer |
| 6,448,065 B2 | 9/2002 | Laugharn |
| 6,448,089 B1 | 9/2002 | Vuong |
| 6,461,490 B1 | 10/2002 | Lennox et al. |
| 6,472,179 B2 | 10/2002 | Stahl |
| 6,478,939 B1 | 11/2002 | Lennox et al. |
| 6,482,593 B2 | 11/2002 | Walt |
| 6,485,918 B1 | 11/2002 | Schermer |
| 6,489,106 B1 | 12/2002 | Shivashankar |
| 6,491,871 B1 | 12/2002 | Fodor et al. |
| 6,545,758 B1 | 4/2003 | Sandstrom |
| 6,548,171 B1 | 4/2003 | Barbera-Guillem |
| 6,558,623 B1 | 5/2003 | Ganz |
| 6,565,813 B1 | 5/2003 | Garyantes |
| 6,569,385 B1 | 5/2003 | Little |
| 6,576,424 B2 | 6/2003 | Fodor et al. |
| 6,576,426 B2 | 6/2003 | Southern et al. |
| 6,586,193 B2 | 7/2003 | Yguerabide |
| 6,600,031 B1 | 7/2003 | Fodor et al. |
| 6,610,482 B1 | 8/2003 | Fodor et al. |
| 6,733,977 B2 | 5/2004 | Besemer et al. |
| 6,785,433 B2 | 8/2004 | Tiefenthaler |
| 6,787,368 B1 | 9/2004 | Wong |
| 6,789,040 B2 | 9/2004 | Kaushikkar |
| 6,800,453 B2 | 10/2004 | Labaer et al. |
| 6,806,361 B1 | 10/2004 | Kajisa et al. |
| 6,862,094 B2 | 3/2005 | Johansen |
| 6,870,627 B2 | 3/2005 | Elkind |
| 6,902,705 B1 | 6/2005 | Caillat |
| 6,911,344 B1 | 6/2005 | Reichert |
| 6,980,294 B2 | 12/2005 | Namba |
| 6,999,175 B2 | 2/2006 | Ivarsson |
| 7,041,208 B2 | 5/2006 | Staats |
| 7,081,954 B2 | 7/2006 | Sandstrom |
| 7,084,980 B2 | 8/2006 | Jones et al. |
| 7,126,688 B2 | 10/2006 | Rassman |
| 7,251,085 B2 | 7/2007 | Bahatt et al. |
| 7,312,069 B2 | 12/2007 | Ban |
| 7,319,046 B2 | 1/2008 | Misiakos |
| 7,463,358 B2 | 12/2008 | Wolf et al. |
| 2002/0024495 A1 | 2/2002 | Lippert |
| 2002/0044893 A1 | 4/2002 | Corn |
| 2002/0068813 A1 | 6/2002 | Dragic |
| 2002/0127565 A1 | 9/2002 | Cunningham |
| 2002/0140938 A1 | 10/2002 | Naya |
| 2002/0197729 A1 | 12/2002 | Tsuzuki |
| 2003/0082820 A1 | 5/2003 | Perbost |
| 2003/0100004 A1 | 5/2003 | Kurz |
| 2003/0107741 A1 | 6/2003 | Pyo |
| 2003/0143576 A1 | 7/2003 | Chao et al. |
| 2004/0008345 A1 | 1/2004 | Nurmikko |
| 2004/0014946 A1 | 1/2004 | Chao |
| 2004/0043384 A1 | 3/2004 | Oleinikov |
| 2004/0048311 A1 | 3/2004 | Ault-Riche |
| 2004/0067597 A1 | 4/2004 | Datwani |
| 2004/0161748 A1 | 8/2004 | He et al. |
| 2004/0174518 A1 | 9/2004 | Naiki |
| 2004/0198637 A1 | 10/2004 | Schultz et al. |
| 2004/0214233 A1 | 10/2004 | Lubman |
| 2004/0248144 A1 | 12/2004 | Mir |
| 2004/0258832 A1 | 12/2004 | Barklund et al. |
| 2005/0002085 A1 | 1/2005 | Matsui |
| 2005/0014179 A1 | 1/2005 | Karlsson et al. |
| 2005/0046848 A1 | 3/2005 | Cromwell |
| 2005/0095577 A1 | 5/2005 | Yang |
| 2005/0200845 A1 | 9/2005 | Nabatova-Gabain et al. |
| 2006/0091051 A1 | 5/2006 | Takada |
| 2006/0134669 A1 | 6/2006 | Casasanta |
| 2006/0154320 A1 | 7/2006 | Zuk |
| 2006/0187459 A1 | 8/2006 | Ok |
| 2006/0234265 A1 | 10/2006 | Richey et al. |
| 2007/0009198 A1 | 1/2007 | Petcavich |
| 2007/0059817 A1 | 3/2007 | Aoyagi |
| 2007/0081163 A1 | 4/2007 | Liang et al. |
| 2007/0099180 A1* | 5/2007 | Robotti et al. .................. 435/5 |
| 2007/0122314 A1 | 5/2007 | Strand |
| 2007/0128455 A1 | 5/2007 | Wolf |
| 2007/0139653 A1 | 6/2007 | Guan et al. |
| 2007/0140918 A1 | 6/2007 | Yin |
| 2007/0222996 A1 | 9/2007 | Guan et al. |
| 2009/0060786 A1 | 3/2009 | Kim et al. |
| 2009/0060787 A1 | 3/2009 | Kim et al. |

FOREIGN PATENT DOCUMENTS

| | | |
|---|---|---|
| WO | WO 93/15110 | 8/1993 |
| WO | WO 95/31480 | 11/1995 |
| WO | WO 96/02830 | 2/1996 |
| WO | WO 96/09547 | 3/1996 |
| WO | WO 97/07593 | 1/1997 |

| | | |
|---|---|---|
| WO | WO 97/41424 | 1/1997 |
| WO | WO 97/41425 | 1/1997 |
| WO | WO 97/12988 | 4/1997 |
| WO | WO 02/052260 | 7/2002 |

OTHER PUBLICATIONS

Kim et al.; U.S. Appl. No. 12/339,017, filed Dec. 18, 2008.

Brockman et al., "Surface Plasmon Resonance Imaging Measurements of Ultrathin Organic Films", Ann. Rev. Phys. Chem., 2000, 51:41-63.

Bogoyevitch et al., "Peptide inhibitors of protein kinases-discovery, characterisation and use", Biochim. Biophys. Acta, 2005, 1754: 79-99.

Eddings et al., "High throughput in situ Biomolecule Analysis Integrating a 3-D Microfluidic Flow Cell Array and SPR Microscopy" Department of Engineering, Chemistry and Mechanical Engineering, University of Utah.

Hines et al., "Bisubstrate analog probes for the insulin receptor protein kinase: Molecular yardsticks for analyzing catalytic mechanism and inhibitor design", Bioorg. Chem., 2005, 33:285-297.

Hu, J.C., et al., "Sequence .Requirements for Coiled-Coils: Analysis with .lambda. Repressor-GCN4 Leucine Zipper Fusions" Science 250:1400-1403 (1990).

Komatsu, et al., "SPR sensor signal amplification based on dye-doped polymer particles" Sci Tech. Adv. Mater., 2006 7:150-155.

Mitchell et al., "Sensitivity enhancement of surface plasmon resonance biosensing of small molecules" Anal Biochem, 2005, 343:125-135.

Qi et al., "Determination of the Bioavailability of Biotin Conjugated onto Shell Cross-Linked (SCK) Nanoparticles", J. Am. Chem. Soc., 2004 126:6599-6607.

Ramachandran et al., "Self-assembling protein microarrays", Science, 2004, 305:86-90.

Severs amd Schasfoort, "Enhanced Surface Plasmon Resonance Inhibition Test (ESPRIT) using latex particles", Biosens. Bioelectron., 1993, 8:365-370.

Shen et al., "Protein kinase structure and function analysis with chemical tools" Biochim. Biophys. Acta, 2005, 1754:65-78.

Wink et al., "Liposome-Mediated Enhancement of Sensitivity in Immunoassays of Proteins and Peptides in Surface Plasmon Resonance Spectrometry" Anal. Chem., 1998, 70:827-832.

International Search Report dated Jul. 3, 2008, Application No. PCT/US06/44957.

International Search Report dated May 10, 2007, Application No. PCT/US06/22123.

International Search Report dated Nov. 10, 2008, Application No. PCT/US08/74865.

Dudek et al.; U.S. Appl. No. 12/061,175, filed Apr. 2, 2008.

Shwoerer et al.; U.S. Appl. No. 12/392,893, filed Feb. 25, 2009.

* cited by examiner

Spin deposition of reactive silane

METHODS FOR MAKING AND USING SPR MICROARRAYS

CROSS-REFERENCE TO RELATED APPLICATIONS

The present application is a divisional of copending U.S. patent application Ser. No. 11/296,659, filed on Dec. 6, 2005; which application is incorporated herein by reference in its entirety.

BACKGROUND OF THE INVENTION

All patents, patent applications, and publications cited within this application are incorporated herein by reference to the same extent as if each individual patent, patent application or publication was specifically and individually incorporated by reference.

The invention relates generally to surface plasmon resonance substrates and associated methods of analyzing biomolecules. In order to analyze a DNA using surface plasmon resonance (SPR) detection, a metal such as gold having a certain thickness is required on the substrate. For application where DNA is deposited on top of gold there is the problem that gold coated glass slides have not been able to survive DNA printing processes that require corrosive oxidizers, with the gold delaminating from the surface. The gold surface must be modified by using different functionalities, the most popular being thiol chemistry. However, the Au—S bonds are vulnerable to aggressive oxidizers used for some DNA printing process. Thus, there is a need for SPR slides that are able to withstand strong oxidizers used in some DNA printing processes.

SUMMARY OF THE INVENTION

One embodiment is an article comprising: a) a substrate; b) a first metal film overlying the substrate; c) a second thin metal film, the second thin metal film having a first surface facing the first metal film, and a second surface opposed to the first surface; and d) a reactive organosilane covalently bonded to the second surface of the second thin metal film through metal-oxygen-silicon bonds. The second surface opposed to the first surface in the second thin metal film is hereafter referred to as the "upper" surface of the second thin metal film. The first metal film may be gold, silver, or copper and the second thin metal film may be Ti, Zr, Al, Cr, Hf, V, Ta, W, or Pb. Typically, the first metal film can generate surface plasmons and the upper surface of the second thin metal film is used to form chemically stable bonds to the reactive organosilane. As used herein the second thin metal film is sufficiently thin so as to allow extension of an evanescent plasmon wave from said first metal film. The resulting chips can be cleaned with aggressive oxidizers and biomolecules such as DNA, RNA, or proteins can be printed on the reactive organosilane. Chemical interactions with the printed DNA, RNA, or proteins can then be monitored through surface plasmon resonance methods. The second thin metal film may also generate surface plasmons that may interact with the surface plasmons or with surface plasmon effects from the first metal film.

Another embodiment is a process comprising: a) depositing a first metal film on a substrate; b) depositing a second thin metal film on the first metal film; c) converting the upper surface of the second thin metal film to the corresponding metal oxide; and d) reacting a functionalized organosilane with the metal oxide, whereby a reactive organosilane is formed on the upper surface of the second thin metal film. The organosilanes used typically have a reactive silane moiety and an organic substituent (i.e., trichloro-organosilanes). The terms "functionalized" and "inert" when used in connection with "organosilane" refers to the organic substituent of the silane and not the silane moiety. Another embodiment is a process comprising: a) depositing a first metal film on a substrate; b) depositing second thin metal film on the first metal film; c) converting the upper surface of the second thin metal film to the corresponding metal oxide; d) reacting an inert organosilane with the metal oxide; e) patterning the inert organosilane to give a pattern of a plurality of metal oxide spots surrounded by inert organosilane; and f) reacting a functionalized organosilane with the metal oxide, whereby a reactive organosilane is formed in the metal oxide spots on the second thin metal film. Another embodiment is a process comprising: a) depositing a first metal film on a substrate; b) depositing a second thin metal film on the first metal film; c) converting the upper surface of the second thin metal film to the corresponding metal oxide; d) applying a patterned photoresist on the upper surface defining a plurality of spots, the upper surface being exposed between spots; e) reacting an inert organosilane on the metal oxide of the upper surface; f) removing the photoresist to form a plurality of metal oxide spots; and g) reacting a functionalized organosilane with the metal oxide, whereby a reactive organosilane is formed in the metal oxide spots. A similar embodiment is a process comprising: a) depositing a first metal film on a substrate; b) depositing second thin metal film on the first metal film; c) patterning a photoresist on the upper surface into a plurality of spots, the surface of the second thin metal film being exposed between spots; d) converting the surface of the second thin metal film between spots to a metal oxide; e) reacting an inert organosilane with the metal oxide of the second thin metal film; f) removing the photoresist to form a plurality of spots comprising the surface of the second thin metal film; g) converting the surface of the second thin metal film in the spots into a metal oxide, whereby a plurality of metal oxide spots is formed; and h) reacting a functionalized organosilane with the metal oxide spots, whereby a reactive organosilane is formed in the metal oxide spots on the second thin metal film.

Another embodiment is a method, comprising a) providing an article including: i) a substrate; ii) a first metal film overlying the substrate; iii) a second thin metal film overlying the first metal film; iv) an organosilane covalently bonded to the exposed upper surface of the second thin metal film through metal-oxygen-silicon bonds; v) a binding group attached to the organosilane; b) contacting the article with a biomolecule; and c) determining whether or not the biomolecule is bound to the binding group by detecting or measuring a surface plasmon resonance signal generated from the first metal film.

DETAILED DESCRIPTION

Figure 1:
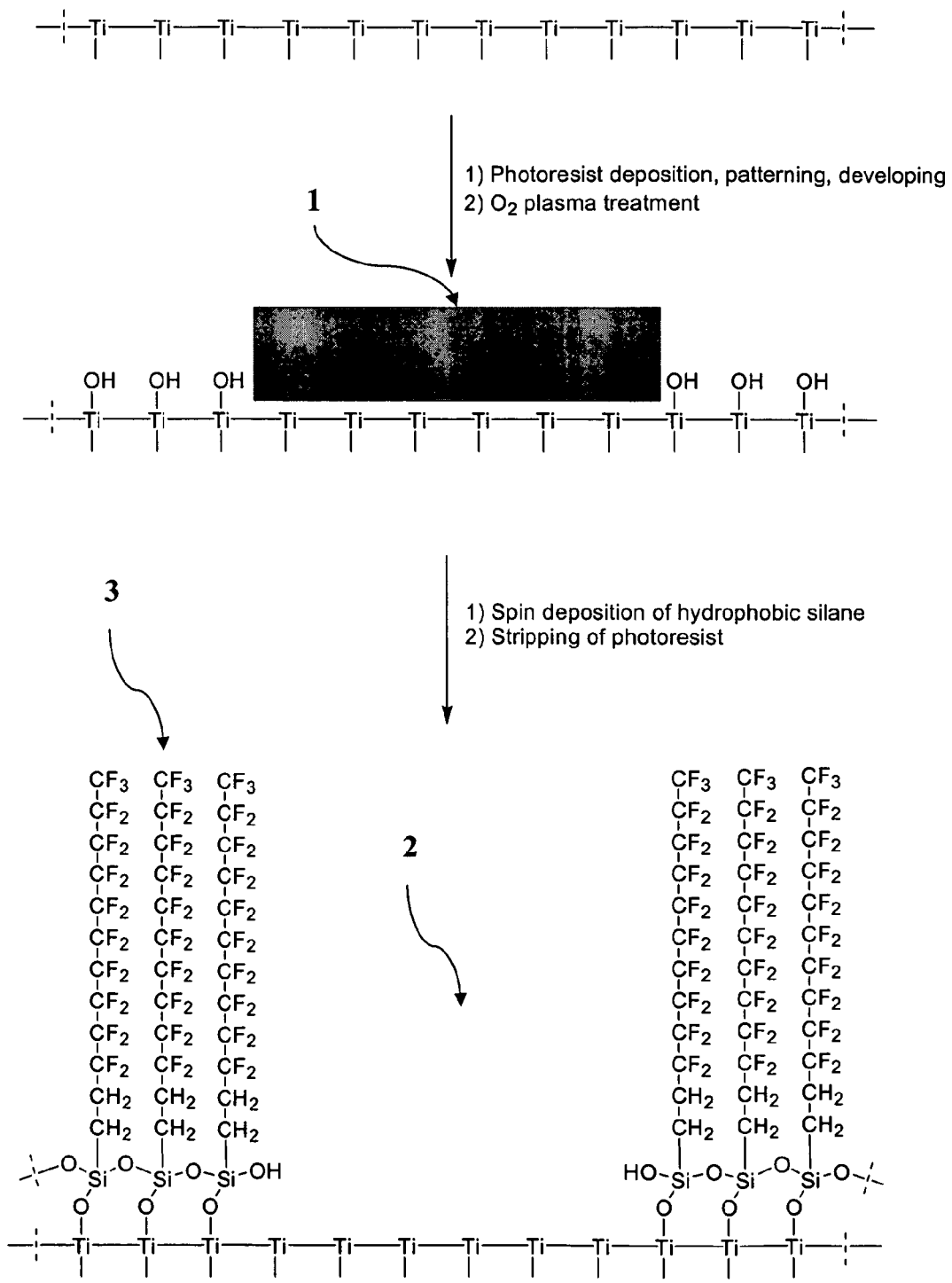
FIG. 1 is a cross-sectional view of a process scheme.

One embodiment is an article comprising: a) a substrate; b) a first metal film overlying the substrate; c) a second thin metal film overlying the first metal film; and d) a reactive organosilane covalently bonded to the upper surface of the second thin metal film through metal-oxygen-silicon bonds. The first metal film may be gold, silver, or copper and the second thin metal film may be Ti, Zr, Al, Cr, Hf, V, Ta, W, or Pb. Typically, the first metal film can generate surface plasmons and the upper surface of the second metal film is used to form chemically stable bonds to the reactive organosilane. When the second thin metal film is sufficiently thin, the evanescent wave of the surface plasmons generated by the first metal film extend through the second thin metal film and can be used to detect chemical changes near the upper surface of the second thin metal film. Detecting these chemical changes can be used, for example, to monitor biological molecule binding and image dielectric thin films. Typically, the substrate is glass or quartz. In other embodiments, the substrate comprises one face of a prism. The article may further comprise an adhesion metal layer between the substrate and the first metal film. The adhesion metal layer typically is Cr, Ti, W, or any combination thereof.

In many embodiments, the reactive organosilane has a pattern on the surface that is a plurality of spots. In most embodiments, the spots are arranged in a microarray. Hydrophobic material may surround one or more of the reactive organosilane spots. The hydrophobic material may cause a polar liquid (e.g., water) to bead on the reactive organosilane spot, which allows the spot to be used as a microwell. The size of each spot is typically 10-1000 μm in diameter, and the density of spots is typically 100 to 1 million spots per square centimeter. The hydrophobic material typically comprises an inert organosilane covalently bonded to the upper surface of the second thin metal film through metal-oxygen-silicon bonds. The inert organosilane may include, for example, a fluorinated alkyl group. In many embodiments, the reactive organosilane comprises hydroxy groups. The hydroxy groups may be capped with DNA or RNA (e.g., DNA or RNA have been reacted with the hydroxyl groups to form covalent bonds). An example of a reactive organosilane comprises the structure

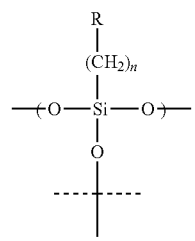

wherein: R is a reactive group and n=1-20. The reactive group R may comprise, for example, the structures

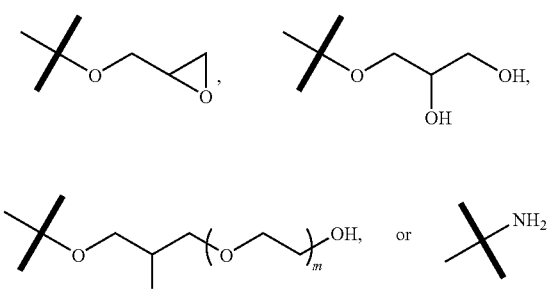

wherein m=1-10. One example of an inert organosilane comprises the structure

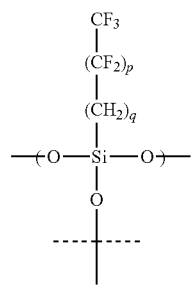

wherein: q=1-4; and p=1-20. In some embodiments, the reactive organosilane comprises the structure

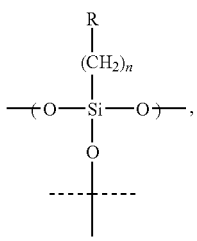

and the hydrophobic material comprises the structure

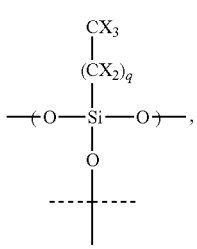

wherein: R is a reactive group; X is independently at each occurrence a hydrogen or halogen; n=1-20; and q=1-20. The reactive group R may be as described above. The distance between the upper surface of the second thin metal film and the reactive group R on the reactive organosilane, and the distance between the upper surface of the second thin metal film and the non-bonded terminus of the hydrophobic material are controlled through the appropriate selection of alkyl (—$(CH_2)_n$—), or haloalkyl (—$(CX_2)_q$—, where X is a halogen) chain lengths.

Another embodiment is a process comprising: a) depositing a first metal film on a substrate; b) depositing a second thin metal film on the first metal film; c) converting the upper surface of the second thin metal film to the corresponding metal oxide; and d) reacting a functionalized organosilane with the metal oxide, whereby a reactive organosilane is formed on the upper surface of the second thin metal film. The first metal film, the second thin metal film, and the substrate may be as described above. In many embodiments, converting the upper surface of the second thin metal film to the corresponding metal oxide comprises oxygen plasma treatment. In one embodiment, the functionalized organosilane is

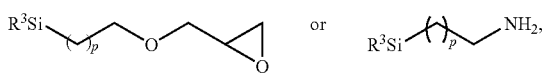

wherein: $R^3$ is chlorine or alkoxy; p=1-20; and the reactive organosilane comprises

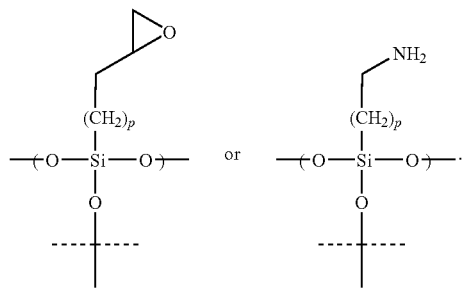

In other embodiments, the reactive organosilane is

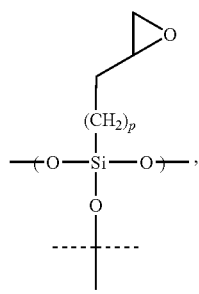

and the process further comprises converting the reactive organosilane to

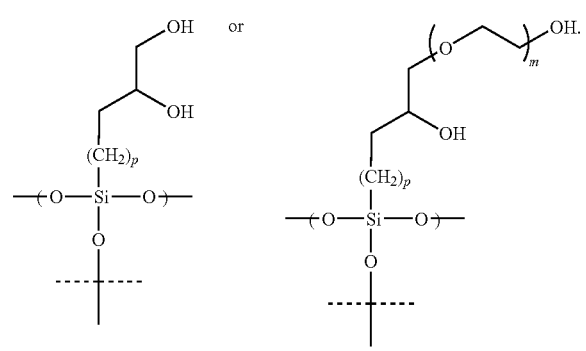

In some embodiments, the process further comprises patterning the reactive organosilane into a plurality of spots. In one embodiment, the process further comprises reacting the reactive organosilane with DNA or RNA.

Another embodiment is a process comprising: a) depositing a first metal film on a substrate; b) depositing a second thin metal film on the first metal film; c) converting the upper surface of the second thin metal film to the corresponding metal oxide; d) reacting an inert organosilane on the upper surface of the second thin metal film; e) patterning the inert organosilane to give a pattern of a plurality of metal oxide spots surrounded by inert organosilane; and f) reacting a functionalized organosilane with the metal oxide, whereby a reactive organosilane is formed in the metal oxide spots on the second thin metal film. Another embodiment is a process comprising: a) depositing a first metal film on a substrate; b) depositing a second thin metal film on the first metal film; c) converting the upper surface of the second thin metal film to the corresponding metal oxide; d) patterning a photoresist on the upper surface into a plurality of spots, the upper surface being exposed between spots; e) reacting an inert organosilane on the metal oxide of the upper surface; f) removing the photoresist to form a plurality of metal oxide spots; and g) reacting a functionalized organosilane with the metal oxide, whereby a reactive organosilane is formed in the metal oxide spots. A similar embodiment is a process comprising: a) depositing a first metal film on a substrate; b) depositing second thin metal film on the first metal film; c) patterning a photoresist on the upper surface into a plurality of spots, the surface of the second thin metal film being exposed between spots; d) converting the surface of the second thin metal film between spots to a metal oxide; e) reacting an inert organosilane with the metal oxide of the second thin metal film; f) removing the photoresist to form a plurality of spots comprising the surface of the second thin metal film; g) converting the surface of the second thin metal film in the spots into a metal oxide, whereby a plurality of metal oxide spots is formed; and h) reacting a functionalized organosilane with the metal oxide spots, whereby a reactive organosilane is formed in the metal oxide spots on the second thin metal film. The substrate, the first metal film, and the second thin metal film may be as described above. The inert organosilane typically includes a fluorinated alkyl group, for example the structure

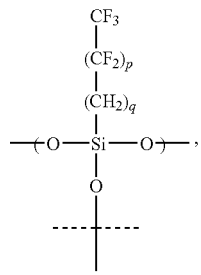

wherein: q=1-4; and p=1-20. The functionalized organosilane and the reactive organosilane may be as described above. In one embodiment, the reactive organosilane is

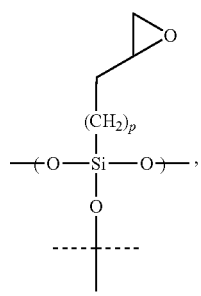

and the process further comprises converting the reactive organosilane to

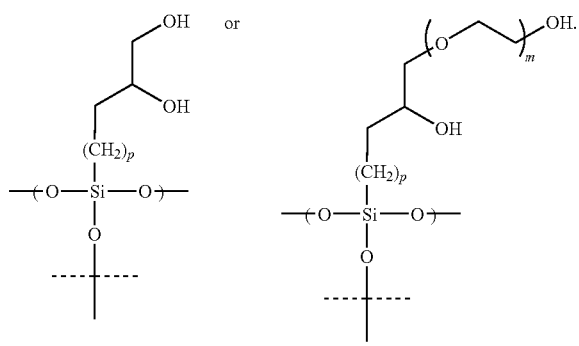

The size of each spot is typically 10-1000 µm in diameter, and the number the density of spots is typically 100 to 1 million spots per square centimeter. The distance between the upper surface of the second thin metal film and the reactive group R on the reactive organosilane, and the distance between the upper surface of the second thin metal film and the non-bonded terminus of the hydrophobic material are controlled through the appropriate selection of alkyl ($-(CH_2)_n-$), or haloalkyl ($-(CX_2)_q-$, where X is a halogen) chain lengths.

Another embodiment is a method, comprising a) providing an article including: i) a substrate; ii) a first metal film overlying the substrate; iii) a second thin metal film overlying the first metal film; iv) an organosilane covalently bonded to the upper surface of the second thin metal film through metal-oxygen-silicon bonds; and v) a binding group attached to the organosilane; and b) determining whether or not the biomolecule is bound to the binding group by detecting or measuring a surface plasmon resonance signal generated from the first metal film. In some embodiments, the binding group comprises DNA or RNA. The biomolecule is typically DNA, RNA, or a protein. In other embodiments, the binding group is an antigen, an antibody, or a hapten. The organosilane may have a pattern of a plurality of spots. The spots may be arranged in a microarray. The size of each spot is typically 10-1000 µm in diameter, and the number the density of spots is typically 100 to 1 million spots per square centimeter. The first metal film, the second thin metal film, and the glass substrate may be as described above.

EXAMPLES

The following example(s) is illustrative and does not limit the Claims.

A glass substrate was cleaned using Diamaflow 688C. The substrate was soaked in a 1% solution of Diamaflow 688C in DI-water (18MΩ) with and sonicated for 5 minutes. After sonication, the samples were brushed in a fresh solution of Diamaflow and DI-water and sonicated again in DI-water at 30° C. in 15 minutes. The substrate was rinsed for 5 minutes and dried with filtered $N_2$ gas. Before the metal deposition the substrate was treated with high pressure $O_2$ plasma for 5 minutes. The plasma cleaning process should happen right before the metal deposition otherwise the surface conditions cannot be precisely controlled. The metal deposition was performed in a Denton Discovery 18 DC magnetron sputtering machine. The base pressure was less than $2 \times 10^{-7}$ Torr. Argon was used as process gas at a pressure of 7.5 mTorr during deposition. The magnetron current was set to 250 mA. First, a 2 nm thick adhesion layer of Cr was deposited followed by deposition of a 47 nm Au layer, followed by deposition of a 10 nm thick layer of Ti.

Figure 2:
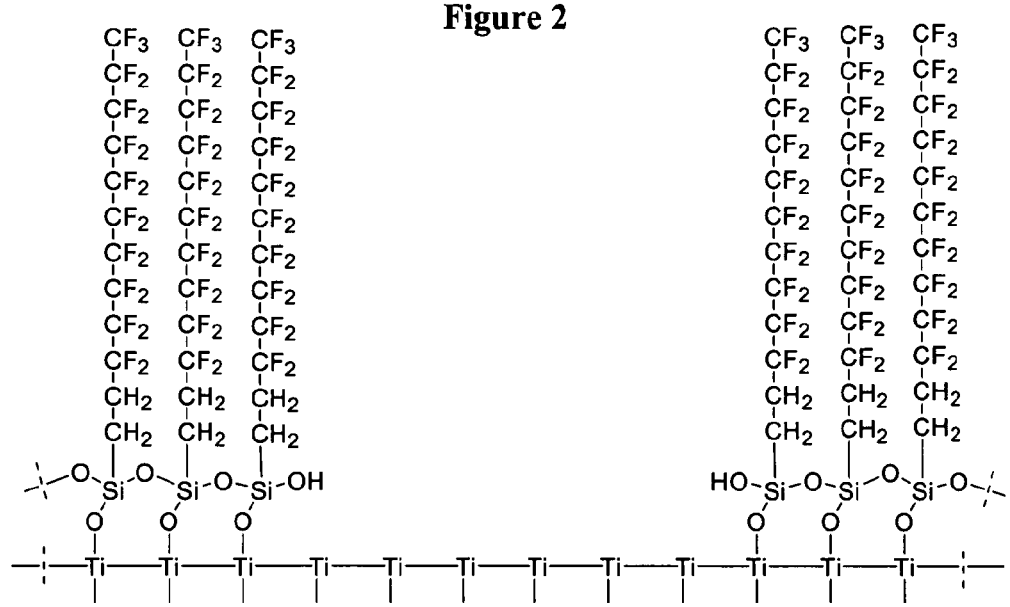
FIG. 2 is a cross-sectional view of a process scheme.
Figure 2:
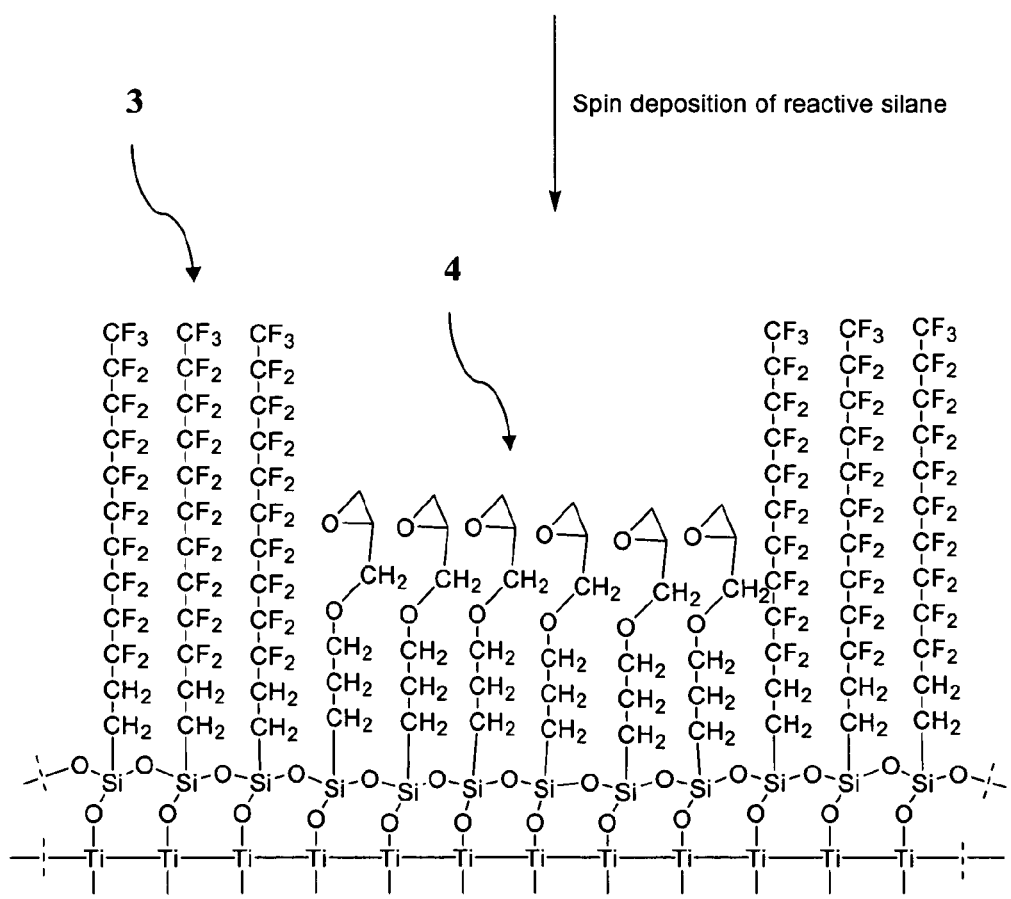
Figure 3:
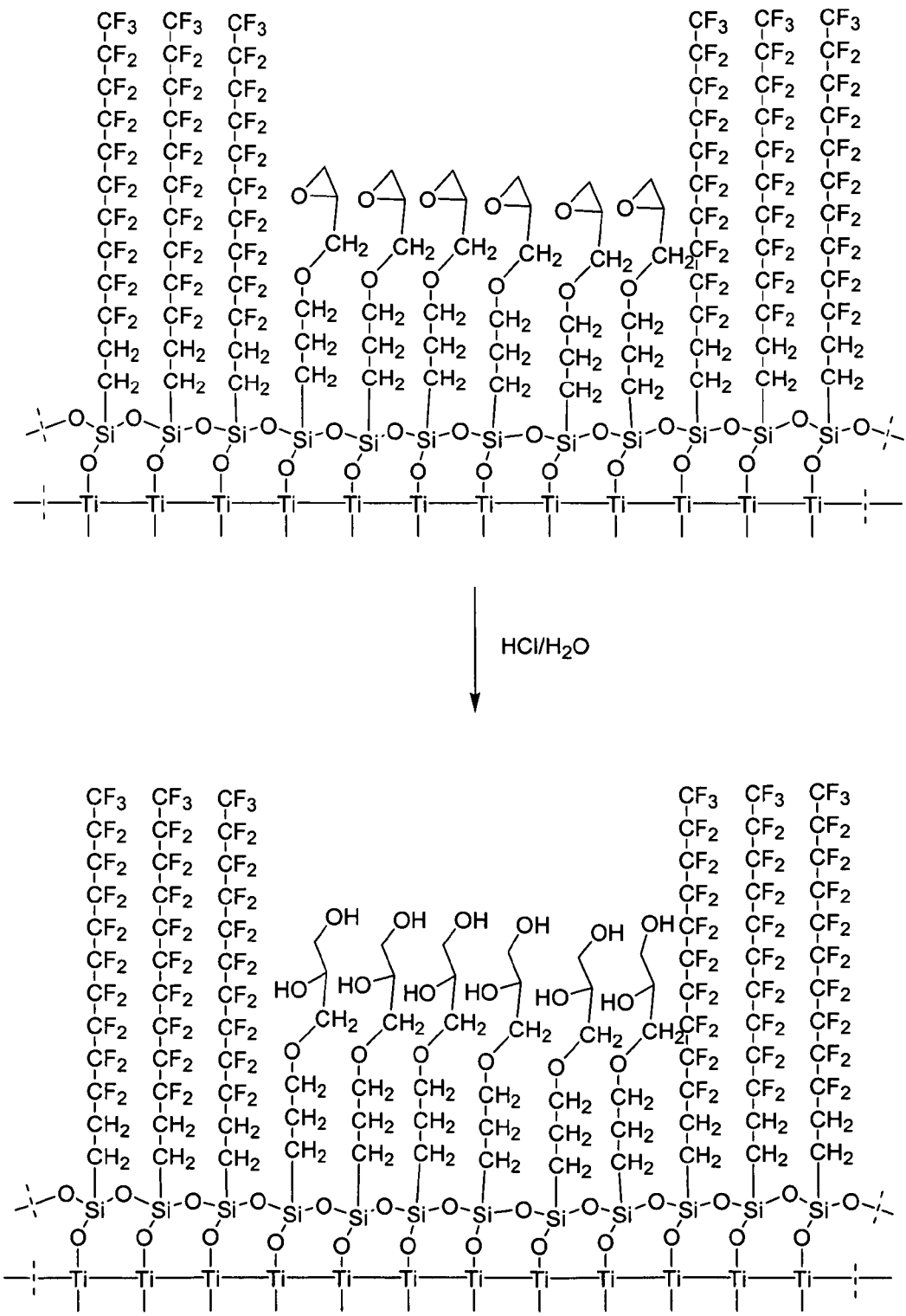
FIG. 3 is a cross sectional view of a process scheme.
Figure 4:
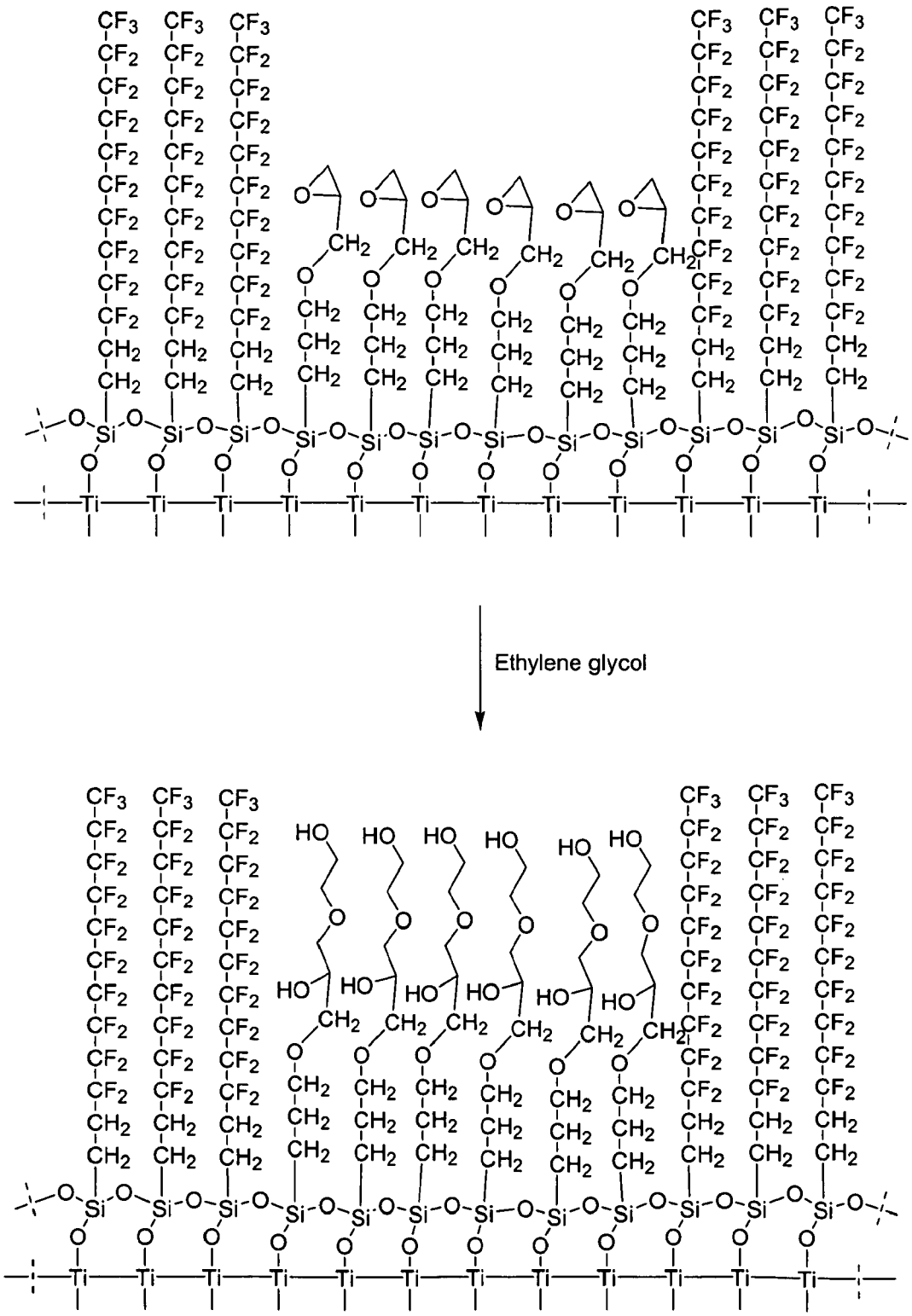
FIG. 4 is a cross-sectional view of a process scheme.

Deposition of the inert hydrophobic organosilane and reactive organosilane are shown schematically in cross section in FIGS. 1-2. After metal deposition the substrate was photolithographically patterned with photoresist (1) squares (100-200 µm on one side). Following development, an $O_2$-plasma treatment was used to enhance the bonding of the hydrophobic silane to the Ti. A solution of 1H, 1H, 2H, 2H perfluoroundecyl trichlorosilane was spin deposited, rinsed with toluene, and dried with $N_2$ gas. The remaining photoresist was removed using a stripper, washed with an isopropyl alcohol and DI-water rinse, and dried with filtered $N_2$ gas. At this point the Ti surface (2) was exposed as a series of spots surrounded by the hydrophobic silane (3). The exposed Ti surface was treated with $O_2$ plasma. (Glycidoxypropoxy)trimethoxysilane was spin deposited as described above for the hydrophobic silane to give the reactive organosilane (4) patterned into series of spots, with each spot surrounded by the hydrophobic organosilane (3). The epoxy-reactive silane was converted to a hydroxy-reactive silane by treatment with $H_2O$/HCl (FIG. 3) or ethylene glycol (FIG. 4).

The invention claimed is:

1. A method of determining binding between a binding group and a biomolecule comprising:
   a) providing an article including:
      i) a substrate;
      ii) a first metal film overlying the substrate;
      iii) a second thin metal selected from the group consisting of Ti, Zr, Al, Cr, Hf, V, Ta, W and Pb, wherein the thin metal film includes a proximal surface and a distal surface, wherein the proximal surface is proximal to the first metal film and the distal surface is distal to the first metal film; and
      iv) the binding group attached to the distal surface of the second thin metal film;
   b) contacting the article with the biomolecule; and
   c) measuring a surface plasmon resonance signal to determine the binding between the binding group and the biomolecule.

2. The method of claim 1, wherein the binding group is selected from the group consisting of DNA and RNA.

3. The method of claim 2, wherein the biomolecule is selected from the group consisting of DNA, RNA, and a protein.

4. The method of claim 1, wherein the binding group is selected from the group consisting of an antigen, an antibody, and a hapten.

5. The method of claim 1, wherein the first metal film is selected from the group consisting of Au, Ag, and Cu.

6. The method of claim 1, wherein the substrate is made from a material selected from the group consisting of glass and quartz.

7. An article for determining binding between a binding group and a biomolecule comprising:
   i) a substrate;
   ii) a first metal film overlying the substrate;
   iii) a second thin metal film selected from the group consisting of Ti, Zr, Al, Cr, Hf, V, Ta, W and Pb, wherein the second thin metal film includes a proximal surface and a distal surface, wherein the proximal surface is proximal to the first metal film and the distal surface is distal to the first metal film; and iv) the binding group attached to the distal surface of the second thin metal film, wherein contacting the article with the biomolecule and measuring a surface plasmon resonance signal determines binding between the binding group and the biomolecule.

8. The article of claim 7, wherein the first metal film is selected from the group consisting of Au, Ag, and Cu.

9. The article of claim 7, wherein the substrate is made from a material selected from the group consisting of glass and quartz.

10. The article of claim 7, wherein the binding group is selected from the group consisting of DNA and RNA.

\* \* \* \* \*